United States Patent [19]
Demetrescu et al.

[11] 4,328,491
[45] May 4, 1982

[54] DYNAMIC DATA DISPLAY SYSTEM, AS FOR USE WITH EEG

[76] Inventors: Mihai C. Demetrescu; Stefan G. Demetrescu, both of 17761 Palmento Way, Irvine, Calif. 92715

[21] Appl. No.: 128,414

[22] Filed: Mar. 10, 1980

[51] Int. Cl.³ .............................................. G06K 15/20
[52] U.S. Cl. .................................. 340/747; 340/720; 340/723; 128/731
[58] Field of Search ............... 340/700, 703, 720, 722, 340/723, 736, 744, 747, 776; 128/731

[56] References Cited
U.S. PATENT DOCUMENTS

3,765,009 10/1973 Graves et al. ....................... 340/747
4,127,849 11/1978 Okor .................................... 340/703
4,222,048 9/1980 Johnson ............................... 340/747

*Primary Examiner*—Alvin H. Waring
*Attorney, Agent, or Firm*—Nilsson, Robbins, Dalgarn, Berliner, Carson & Wurst

[57] ABSTRACT

A dynamic display system for discrete events of complex data carried by discrete electrical signals which indicate values in three coordinates as triads. One of the values may be an independent variable, e.g., time. A cathode ray tube display apparatus is actuated by format signals to exhibit a pictorial three-dimensional perspective field of reference somewhat in the figure of an elongate box. The discrete electrical signals representative of data are processed to develop display signals to provide representative images in the field of reference. Specifically, the data events or elements are manifest in the form of lines or linear symbols that indicate coordinate values by symbol height and position. The independent variable, time, is scaled from an origin line in the field of reference to extend along the depth of perspective so that the linear symbols advance along the path of perspective to accomplish a dynamic display with the illusion of motion. The specific system herein displays EEG waves, indicating the magnitude and frequency of individual brain waves with respect to time of occurrence to provide a marching display of both present and recent past information in chronological order. Data may be recorded and later played back. Furthermore, color is utilized in the display to the ranges of frequency. A conventional television format is employed in which the linear symbols are formed along scanning lines of the television raster pattern.

21 Claims, 8 Drawing Figures

DYNAMIC DATA DISPLAY SYSTEM, AS FOR USE WITH EEG

BACKGROUND AND SUMMARY OF THE INVENTION

With the continued availability and accumulation of data in almost all fields, a growing need exists for data display systems that are capable of representing a substantial quantity of information in a readily perceivable form. Dynamic operation is important for such a system either to scan through data or to monitor real time data. The electroencephalogram (EEG) is exemplary of valuable data which is often ignored because traditionally it has not been available in a form that is readily perceivable. Specifically, the EEG is essentially a wave form that is representative of electrical variations occurring between distinct locations on the human head. The wave form depicts a non-periodic stochastic phenomenon. As is very well known in several fields of medicine, the EEG contains valuable data; however, the absence of recurring patterns in the wave form considerably complicates its analysis as for diagnostic use. Consequently, in the past the use of EEG has been relatively limited. In that regard, a significant advancement in creating a record of such data is disclosed in U.S. Patent Application Ser. No. 973,423, filed Dec. 26, 1978, and entitled APERIODIC ANALYSIS SYSTEM, AS FOR THE ELECTROENCEPHALOGRAM by Mihai C. Demetrescu, subsequently maturing into U.S. Pat. No. 4,215,697.

In the system of the referenced patent, the data of an aperiodic wave form is compacted to present a substantial interval of analog signal in a single picture. Essentially, as disclosed in detail in the patent, data is manifest to indicate characteristics of the EEG, which have come to be known in the field of EEG as waves (and spikes). Specifically, the amplitude of a wave of EEG, for example, is manifest as the height of a line or bar which appears in pictured three-dimensional coordinates. The three-dimensional coordinates may be indicated on a plane surface with the traditional format and symbols, X (horizontal), Y (vertical), and Z (depth). The amplitude of the wave is scaled to the vertical or Y coordinate, equivalent frequency (wave period) is indicated by horizontal displacement, and time is referenced to the depth or Z axis. By using such a format, several minutes of EEG recording can be represented on a single page.

While improved techniques for analyzing and displaying complex data as indicated above, have advanced the practicality of utilizing various data, e.g. EEG, a need has continued to exist for improving the display of the data in a perceivable form, particularly as in cases where real-time events are being monitored or a substantial period of data is to be progressively reviewed. That is, from a computer graphics point of view, a need has existed for an economic system to window complex data progressively, as with regard to time, so as to provide a dynamic display of selected data in a simple, perceivable form.

In general, the present invention is directed to a dynamic display system for presenting data as it is progressively windowed, for example, with reference to real time. Four dimensions (three spatial and one color) are defined by a reference field to graphically define data events on a two-dimensional surface as afforded by a television monitor. One of the spatial dimensions, for example, the depth or Z dimension of the reference field may be scaled to the independent variable, e.g., time, to accomplish a dynamic display, or progressively window select data.

A system of the present invention has been embodied to dynamically display EEG information in real time and with several minutes of data concurrently displayed. Waves of the EEG are presented as lines, the height (Y) of which are scaled to wave amplitude. The period of each wave (equivalent frequency) is indicated in a second spatial dimension (X), while time is indicated in a third dimension (Z). In the operating embodiment, time is progressive to develop the illusion of the data moving rearward along the line of perspective or Z dimension. Also, in the operating embodiment, color is utilized to stress the distinction between waves of different equivalent frequency ranges. The display is developed by a traditional television raster scan pattern which is critically oriented so that scanning lines conform to the symbol lines or bars to obtain clear definition.

BRIEF DESCRIPTION OF THE DRAWINGS

In the drawings, which constitute a part of the specification, exemplary embodiments demonstrating various objectives and features hereof are set forth as follows.

DESCRIPTION OF THE ILLUSTRATIVE EMBODIMENT

As indicated above, detailed illustrative embodiments are disclosed herein. However, systems for developing various dynamic displays may be embodied in various forms, some of which may be detailed rather differently from the disclosed embodiments. Consequently, specific structural and functional details disclosed herein are merely representative, yet in that regard, they are deemed to afford the best embodiments for purposes of disclosure to provide a basis for the claims herein which define the scope of the present invention.

Figure 1:
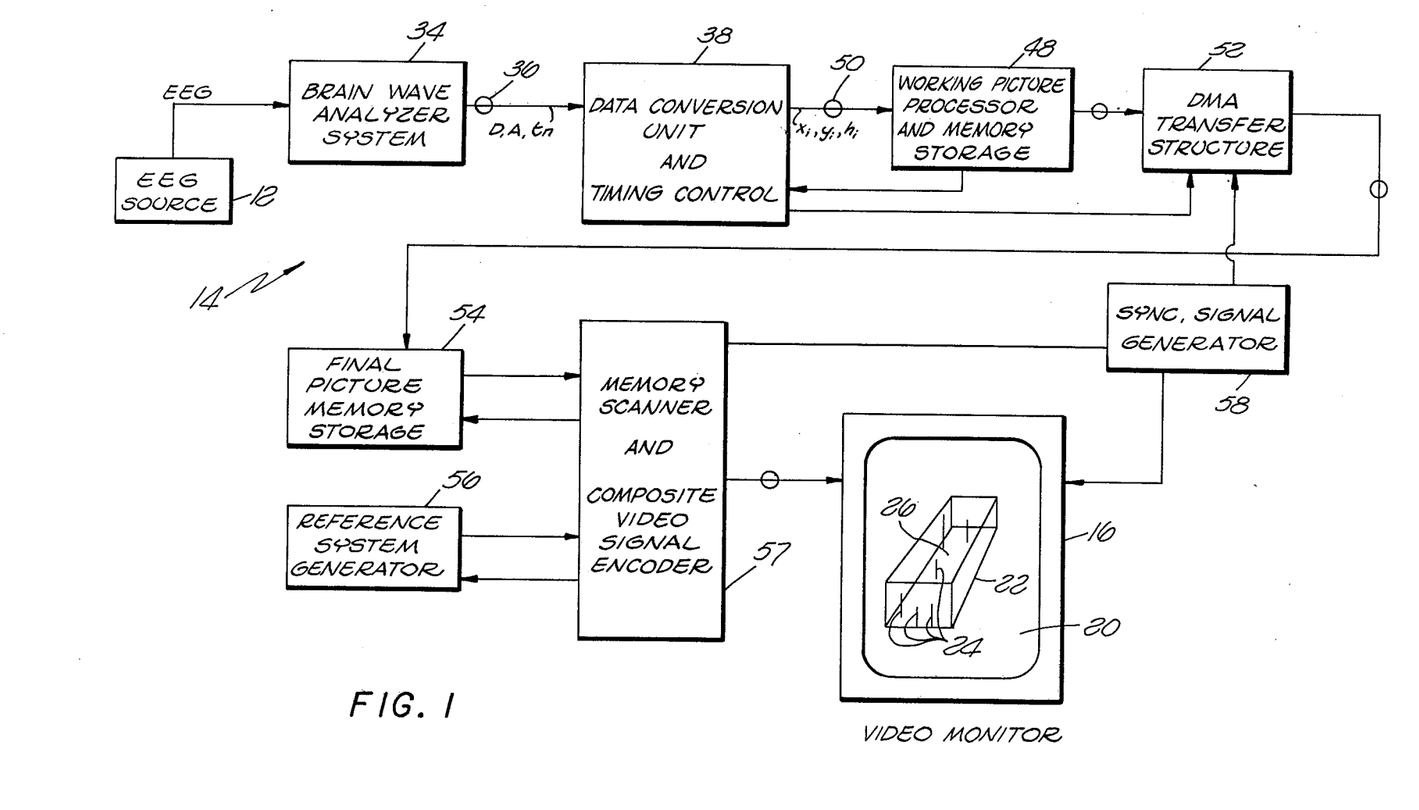
FIG. 1 is a block diagram of a system constructed in accordance with the present invention and showing a simplified exemplary display.

Referring initially to FIG. 1, a system of the present invention is depicted for a dynamic visual presentation of an EEG. That is, as fresh data is considered, the display is changed to give the illusion of a moving data field.

An EEG source 12 is represented in FIG. 1 which may take any of a variety of forms to provide a classic wave form of the electroencephalogram, the elements of which comprise useful medical data. The EEG source 12 is connected to a multiple-block processing system, generally indicated at 14, the output from which is supplied to a television or video monitor 16 (lower right). The plane face 20 of the monitor exhibits a display consisting of a field of reference or perspective box 22 and data symbols, i.e., lines 24.

Waves of the EEG are indicated by the data lines 24; their amplitude and position manifesting the character of such waves. Prior to considering the waves represented by the lines 24 in greater detail, it is perhaps noteworthy that substantial work has been done in the area of EEG analysis and that certain terminology and definitions have been adopted. For example, the subject is treated at length in a book entitled "Monitoring in Anesthesia," edited by L. J. Saidman and N. T. Smith, published by John Wiley & Sons, Inc., 1978.

In accordance with traditional EEG analysis, a wave is considered as a portion of the wave form occurring between two negative peaks or bottoms in the EEG. On the basis of its period or duration, a wave may be assigned an equivalent frequency. The period or the equivalent frequency of individual waves accordingly constitutes one dimension that is deemed to be important in EEG analysis. Another important dimension for such analysis involves the amplitude of a wave. The instant when a wave occurs, either in a real time or within a sequence, is also a significant dimension. Thus, as disclosed in the above-referenced patent, an EEG is processed by an analyzer to provide a triad of digital signals representative of three dimensions that characterize each wave, i.e., equivalent frequency, amplitude, and time of occurrence. The triads of information are supplied from the analyzer and, as disclosed in the referenced patent, are plotted on three-dimensional coordinates. It is noteworthy that the system of the present invention utilizes a similar technique for analyzing the EEG; however, the nature of the display and the processing of the triads is completely different.

Consideration will now be given to the format of the display on the face 20 of the monitor 16. As indicated above, the perspective box 22 provides a graphic field of reference for a dynamic display with the illusion of motion. While the perspective lines defining the sides and ends of the box 22 remain stationary, the dynamic nature of the display results from the apparent motion of the bottom 26 of the box. In one sense, the bottom 26 of the box 22 may be analogized to a moving rug. It might also be likened to a moving belt carrying the linear data symbols or lines 24 backward along the line of perspective to indicate their displacement with regard to the independent variable, e.g., time. That is, with the passage of time, for example, the data lines 24 in the display move backward from an origin line and the viewer, along the line of perspective. In that sense, the aging data accommodates human perception with relative ease being manifest in a logical and natural format.

The display appearing on the face 20 of the monitor 16 might be considered as a stack of data slices each of which progressively moves rearward along the line of perspective. As a slice representative of new data is formulated, it appears at the front of the box 22 in a location of origin then with the passage of time (the independent variable) it incrementally moves rearward (as though on a conveyor belt) until it occupies the last position in the box 22 immediately prior to dropping out of the display. Further explanation of the display in this sense will now be related to FIG. 2 which shows a single slice S of data as it appears at three different instants of time.

Figures 2, 3, 4, 5, 6:
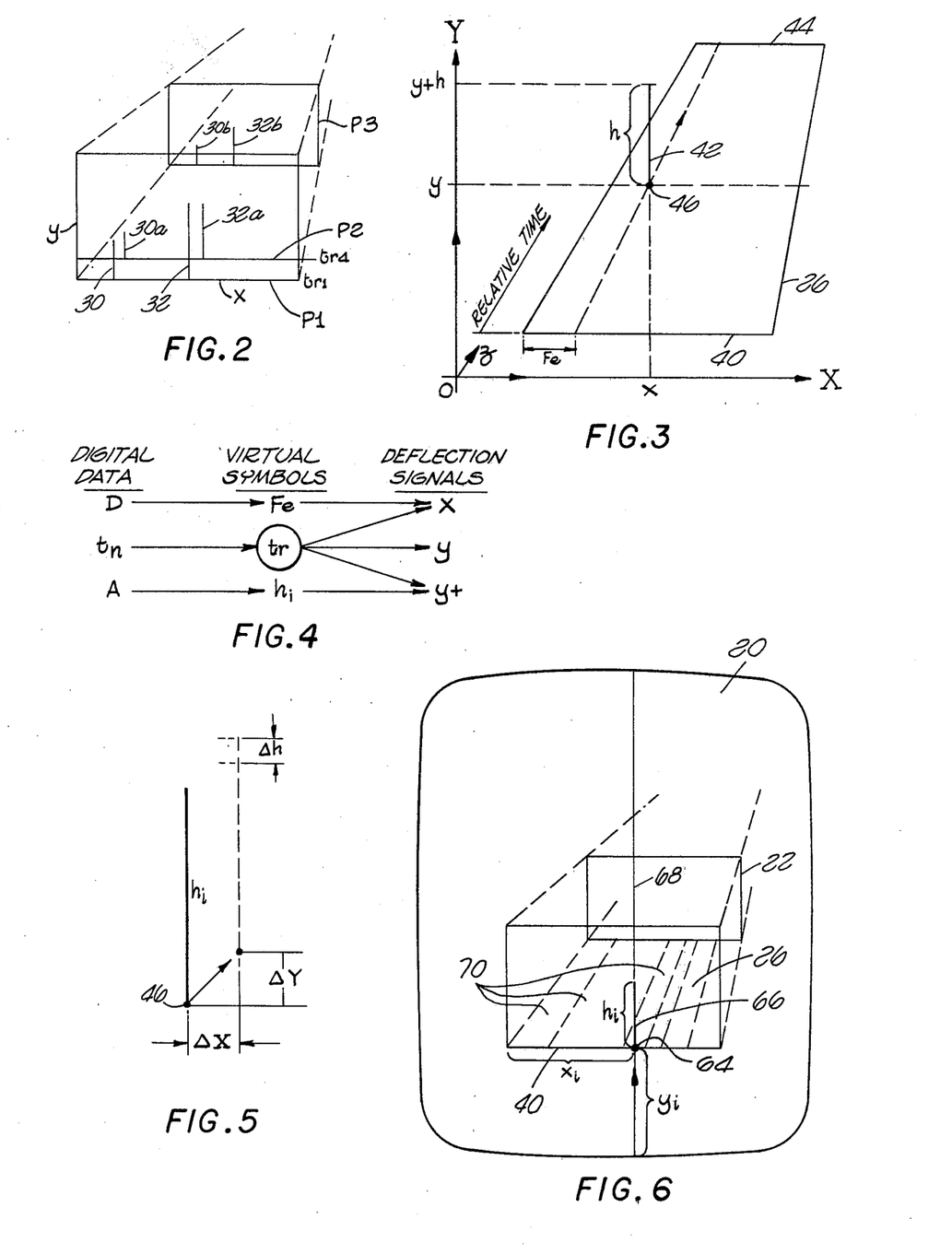
FIG. 2 is a fragmentary graphic representation employed for explaining the display developed by the system of FIG. 1.
FIG. 3 is a graphic analysis of certain coordinates in the display of FIG. 1.
FIG. 4 is a diagram illustrative of the signals representative of data triads and the processing of such signals.
FIG. 5 is a diagram illustrating the change of a symbol in the display of FIG. 1 with change in the independent variable, e.g., time.
FIG. 6 is a plane view of a simplified dimensional display as developed in the system of FIG. 1.

First consider the representation of a fresh data as a new slice S appears at position P1, the origin location, and in time, the stage for fresh data. For simplicity, the exemplary data slice indicates only two waves which are manifest by the lines 30 and 32. The height of the lines 30 and 32 (in the Y dimension) indicates the amplitudes of the represented waves. The position of the lines 30 and 32 on the horizontal axis (X) indicates the equivalent frequency or period of the waves.

Immediately after the signals representing the data are processed to provide a presentation, the fresh slice (containing) lines 30 and 32) appears at the initial position P1 illustratively representative of a relative time tr1 in box 22. From the position P1 at the origin line, the represented data slice S will move rearward with time along the line of perspective diminishing in size to conform with the perspective box 22. Specifically, at a later time, designated as tr4 with respect to the relative time in box 22, the data slice S is at the position P2, indicating to the viewer the fact that four seconds have elapsed since the slice of data (which occurred at absolute time t1) has entered the display. Still later at the time designated tr18, which is 18 seconds since the occurrence of the symbols, the slice is at P3. Of course, the absolute time designation of the slice remains t1 throughout. Thus, to coordinate time with position in the perspective or depth dimension Z, each data slice moves rearward with time.

It is to be understood that the presentation of FIG. 2 illustrates only three positions in the progressive displacement of a single slice S of data moving rearward along the line of perspective. However, in an actual display of an operating system, each time position, say from tr1 through tr240, is occupied by a data slice. Thus, a representation is accomplished which is suggestive of a conveyor belt or a moving rug with the bottom 26 (FIG. 1) of the display transporting the symbols or lines rearward along the field of reference defined by the perspective box 22. In summary, the most current data is represented by the foremost slice in the box, e.g., the slice in position P1 (FIG. 2). The oldest data slice occupies the deepest position in the box 22 (FIG. 1) and after its interval of display, it is dropped from the presentation. In one operating embodiment of the present invention, the Z axis (depth) encompasses a period of four minutes so that significant EEG data of that period is simultaneously presented to the viewer.

The display of the present invention affords several distinct advantages. First, the provision of a real-time display (with history moving into the background) effectively depicts events in a readily perceivable form. Also, the provision of fresh data against the background of older data provides the observer with comparative information for promptly detecting changing patterns in the data. As another consideration, the use of perspective scaling in the data equates so completely with human optical perception that little training or experience is required for effectively analyzing data from the display of the present invention.

With the above explanations in mind, it is now deemed appropriate to pursue some further details of the composite system 14 for developing the display as described. The EEG source 12 (FIG. 1) supplies a representative electrical signal to a brain wave analyzer system 34. Functionally, the system 34 senses the occurrence of waves (and spikes) in the EEG, and formulates representative signals in a digital format. Specifically, the system 34 presents signals representative of a triad of values descriptive of each wave (or spike) in the EEG. Each triad takes the form of three digital signal representations for values D, A and tn. The signals D manifest the duration or period of the wave while the signals A indicate the wave amplitude. The signals tn manifest the absolute time of occurrence of the wave. As suggested above, and throughout the description, the term "wave" will be used generically to include either a wave according to the classic definition, or a spike. Again, an operative form of the brain wave analyzer system 34 is shown and described in the above referenced patent. Functionally, the system 34 provides sets of signals representative of wave triads which pass through a cable 36 to a data conversion unit 38 incorporating timing control. The function of the unit 38 is to process the triads (represented by signals D, A and tn) to another form for eventually driving the monitor 16 to accomplish the display as described above. In that regard, as explained above, it will be appreciated that the display develops a three-dimensional presentation on a two-dimensional surface, i.e., the face 20 of the monitor 16. At this state, reference to FIG. 3 will be helpful in understanding the transitional processing of the signals.

From an origin point 0 (lower left, FIG. 3, not in display) two-dimensional coordinates are indicated along a horizontal (X dimension) and a vertical (Y dimension). In a sense, these two-dimensional planar coordinates are compatible with the three-dimensional coordinates X and Y of the display. Specifically, the two-dimensional coordinates are appropriate to the three-dimensional display with scaling to accommodate the perspective display in the field of reference.

For simplification, only the bottom 26 of the perspective box 22 (FIG. 1) is indicated in FIG. 3. Relating the above explanation to FIG. 3 and recapitulating to some extent, the forward edge 40 of the bottom 26 defines both an origin location for the Z dimension (time) and the X coordinate in the three-dimensional system. In a related fashion, vertical distances are scaled in relation to the Y coordinate. Specifically, an illustrated representative symbol 42 has a height (indicated by the letter h) which is scaled to indicate the amplitude of a wave. Thus, amplitude is indicated by the height of symbols while their horizontal displacement indicates period or equivalent frequency.

With the passage of time, symbols move along the depth axis Z by shifting from the forward edge 40 of the bottom 26 to a rear edge 44. As suggested above, certain adjustments are necessary to accomplish that displacement while preserving the perspective in the field of reference or box 22 as suggested by the bottom 26. Specifically, as the symbol 42 moves rearward on the bottom 26, its position and height must change to preserve perspective. The symbol (remaining vertical) must be displaced to the right as it is moved upwardly. A similar adjustment (to preserve perspective) necessitates that the height or length of the symbol (designated h) must diminish in moving away from the viewer. Generally, such adjustments are made for each of the symbols in each data slice prior to shifting a data slice rearward in the display by the working picture processor 48 (FIG. 1). Thus, symbols are initially processed for presentation in the foremost data slice by the data conversion unit 38 (FIG. 1), then subsequently processed by unit 48 to reflect time by perspective deviation as the slice moves rearward. Ultimately, the symbols are dropped from the presentation after passing the edge 44 (FIG. 3).

Processing the data triads to develop display control signals involves changes which are best explained somewhat graphically. Accordingly, reference will now be made somewhat simultaneously to FIGS. 3 and 4.

The data triads from the system 34 (FIG. 1) comprise the signals D, A and tn. The signals of the triad are indicated in the first column of FIG. 4 as the triad of values defining a discrete event, i.e., wave. The signal D manifests a value indicating the period of a wave, which is directly related to horizontal displacement in FIG. 3. Specifically, in the three-dimensional field of reference, the equivalent frequency of the symbol 42 is indicated by the horizontal distance Fe, recognizing that the distance appears to vary slightly with time as the symbol 42 moves rearward on the bottom 26. Somewhat similarly, the signal A representative of an amplitude value is linearly related to the value h defining the height of the symbol. Again, with the progression of time and the resulting displacement of the symbol 42, the height h is reduced with perspective change. Finally, the signal tn indicates a value designating the time when a wave occurred. As indicated in FIG. 4, the time signal tn is processed to provide a signal tr, indicative of the relative time the symbol occupies in the picture (i.e., the time since it first entered the picture). It is this relative time tr which is scaled in the depth or Z dimension of the display.

The signal processing develops deflection signals as related to beam displacement in a television display as is well known in the art. Essentially, the display signals simply identify the location of the base 46 of the symbol 42 and the height h of the symbol 42. Consequently, the deflection signals may be seen to be as represented in the third column of FIG. 4, specifically, x, y and y+h, which are the physical magnitudes resulting from processing of the virtual symbols represented in the second column of FIG. 4.

At this point in the description, it is noteworthy that the symbol 42 coincides with or aligns on the path of a scanning line of the raster pattern employed in the monitor 16 (FIG. 1). That is, the raster pattern, as well known in television, scans the face of the display to trace out the desired image. Essentially, scanning lines (conventionally horizontal) are interconnected by blanked retrace lines. However, in the present system, the display is rotated so that the symbols align with the scanning lines, now oriented vertically. As a consequence, the deflection notation is reversed from that of traditional television notation. Specifically for example, the vertical symbol 42 (FIG. 3) encompasses a fragment of a "horizontal" deflection line in the monitor 16, the display actually being with the monitor 16 positioned on its side. The benefits of such an orientation will be further evident after considering the detailed description set forth below; however, note that as the signals x and y designate the base 46 (FIG. 3) where the beam is unblanked, the only information required to complete the symbol 42 is the blanking location (top of the symbol 42). That location is specified by the signal h.

In deriving the deflection signals x, y and h, the value of time tr acts to modify all three values. That is, as the symbol 42 moves rearwardly on the bottom 26, it does so in perspective. Therefore, as suggested above, the values of $x_i$ and $y_i$ are both modified to reflect perspective displacement and the value of $h_i$ is modified to reflect a shortening of the symbol 42.

The modifications of the symbol 42 are illustrated somewhat more succinctly in FIG. 5. Specifically, as the symbol moves rearward in the box (i.e., as tr increases), it is displaced from the position illustrated as a solid line (its initial position) to that indicated in dashed line. It will be apparent that the base 46 is displaced in both coordinates, i.e., x and y, and the symbol is shortened by Δh. It is noted however that in accordance with the laws of perspective presentation, the differentials are not linearly proportional with offset along the Z axis.

Returning now to the system as depicted in FIG. 1, as indicated above, the brain wave analyzer system 34 provides information or triads of magnitude or value, each of which is represented by signals to characterize a specific wave. The triad data signals are applied from the system 34 through the cable 36 to the conversion unit 38 which provides signals indicative of deflections $x_i$ and $y_i$ (defining the initial location of the base for a symbol) and $h_i$ (defining the initial height of the symbol). Such signals are processed for the first or foremost position in the referenced box 22. Specifically, scaling the base point (x and y deflection) for symbols in the first slice position simply involves arithmetic operations to accommodate marginal displacement. That is, the equivalent frequency of a symbol (resulting from the signal D) is simply displayed in scaled alignment on the leading edge 40 (FIG. 3). As the first time or slice position indicates current data, it coincides with the leading edge 40. The determination of the height $h_i$ of the symbol 42 (period of unblanking) is directly related to the amplitude signal A. Accordingly, the operation is simply to scale the value of the signal A to form the signal $h_i$ for the first display slice. These operations are performed by well-known arithmetic manipulations in the conversion unit 38 to produce the signals $x_i$, $y_i$ and $h_i$ (representing the similarly named data) supplied through the cable 50 to a working picture processor and memory storage 48.

The processor and storage 48 performs the computation on individual symbols in individual slices to accomplish presentation and shifting the slice rearward in the display. Essentially, the computation involves the manipulations as explained above with reference to FIGS. 3 and 5 along with processing for the display format.

When the working picture processor and memory storage 48 has completed the computations for a display, representative digital signals are supplied through a direct memory access transfer structure 52 to a final picture memory storage 54. In synchronism with the scanning operation of the monitor 16, a memory scanner and encoder 57 scans digital signals from the storage 54 and converts the signals to a video or analog form. Such signals are mixed with reference field signals from a generator 56 that accomplish the box 22 in the display. Of course, it is necessary to synchronize the operation of the entire system to the operation of the monitor. Consequently, a synchronizing signal generator 58 is connected to provide sync signals to the video monitor 16 and also to provide timing signals to the structure 52 and to the scanner and encoder 57.

In view of the above preliminary description, the operation of the system of FIG. 1 may now be best explained by assuming certain conditions and pursuing the responsive operations resulting from such conditions. Accordingly, assume that a sequence of EEG is presented by signals from the EEG source 12 which account for a single slice in the data display and during such an interval, assume further that a single wave has occurred having an equivalent frequency of 18 hertz. As a consequence of that occurrence, the brain wave analyzer system 34 provides signals D, A and tn, which indicate respectively the duration, amplitude, and time of occurrence of the wave. Of course, the time of occurrence is related to real time.

The signals D, A and tn are implicit in carrying the data of virtual symbols diagramatically and symbolically described with reference to FIGS. 3 and 4. Somewhat more explicitly, the signals D, A and tn simply are translated to deflection signals $x_i$, $y_i$ and $h_i$. Deflection signals are developed to accomplish the desired display of the slice appearing at the foremost position in the box 22 (FIG. 1). Such a slice is illustrated at the forefront of the display depicted in FIG. 6 to which reference will now be made.

Utilizing the data implicit in the signals D, A and tn, signals $x_i$ and $y_i$ are formulated to locate the base point 64 for the symbol 66 on the monitor face 20. The data translation will be apparent to one skilled in the art in the sense that the signal D (indicating equivalent frequency which is the arithmetic conversion of the duration of the wave) arithmetically translates to a signal $x_i$ indicating the scanning line in the raster pattern on which the point 64 initially falls. It will be apparent that the translation simply involves scaling the equivalent frequency value of eighteen so that the base point 64 falls onto the leading edge 40 of the box 22 wherein the foremost slice appears. Accordingly, the signal $y_i$ may be seen to be constant in that the point 64 will lie in coincidence with the leading edge 40 on the scanning line 68. A relatively simple computation is involved based upon the coincidence of the scanning line 68 with the leading edge 40. Additionally, the value of the signal $h_i$ is determined in direct relationship to the information signal A indicating the amplitude of the wave. Accordingly, this processing is simply a matter of scaling. Thus, in the data conversion unit 38, the initial values are determined for signals $x_i$, $y_i$ and $h_i$ which signals are provided through a cable 50 to the working storage 48. Of course, the data of a slice may involve several waves; however, for simplicity of explanation, a single wave has been assumed.

The memory storage of unit 48 includes a considerable number of storage bins divided in two sets as will be disclosed in greater detail below. Each bin of the first set receives from the data conversion unit 38 the signals $x_i$, $y_i$ and $h_i$ for all wave in a particular data slice. That is, bins are allotted to data slices and accordingly, they register signals representative of the waves for each registered data slice. Utilizing such organization, as described in greater detail below, the bins are shifted in time significance to accomplish the marching display as described above so that the data slices apparently move from foremost to rearmost in the reference display box 22 (FIG. 1).

From the first set of memory storage bins in the working picture memory storage 48, the signals are processed to arrange them in a sequence coinciding to their order of appearance in the raster scanning pattern. That is, as indicated above, the scanning line 68 (FIG. 6) simply coincides to a portion of one line of a conventional television raster pattern scanned over the face 20 of the monitor 16. Consequently, the individual signals x, y and h (derived from $x_i$, $y_i$ and $h_i$ as per FIG. 5) are rearranged from the slice-sequence of the first set of storage bins (in storage 48) to the scanning sequence in which the defined base points appear in the raster pattern consisting of generally-parallel lines as represented by the line 68, and stored in the second set of storage bins of unit 48. The detailed structure of the processor 48 is treated below.

From the processor 48, the scanning sequence signals x, y and h are supplied through the direct memory access transfer structure 52 to the final memory storage 54 each time an updated image is brought into the dynamic display. Such signals are scanned from the storage 54 by the scanner and encoder 57 for conversion to an analog or video format, as well known in the prior art, to be combined with signals representing the static field of reference or box 22. The complete operation is sequenced by the signal generator 58 so that the composite video signal is supplied to the monitor 16 in synchronism with the fixed scanning pattern to accomplish the display on a frame by frame basis.

At this point, it is to be noted that the bottom 26 of the referenced box 22 (FIG. 6) is color coded to emphasize the distinction between originating points of symbols representing waves of different equivalent frequency. Specifically, each of a series of bands 70 extending somewhat parallel in the perspective of the bottom 26 is manifest in a different color so as to emphasize the frequency distinction of individual waves. Also note that the actual symbols (e.g., the symbol 66) are uniformly of the same color as the band 70 in which they originate. Of course, the symbols are far brighter than the background 26, the scanning beam being unblanked to a greater degree while they are formed.

The determination of the color for a symbol (e.g., symbol 66) is resolved in the processor 48 by simply including a table which provides a signal c indicative of the appropriate color based upon the value of the signal $x_i$. This signal c is transferred along with the x, y and h signals by the transfer structure 52 to the final storage 54. When unit 57 scans the latter, the color information becomes also available for being encoded in the composite video signal. Thus, immediately prior to the display of each symbol, the signal c is consulted, the color is established and in accordance with well-known television techniques, the monitor 16 is driven to establish the predetermined color for the symbol.

Figure 7:
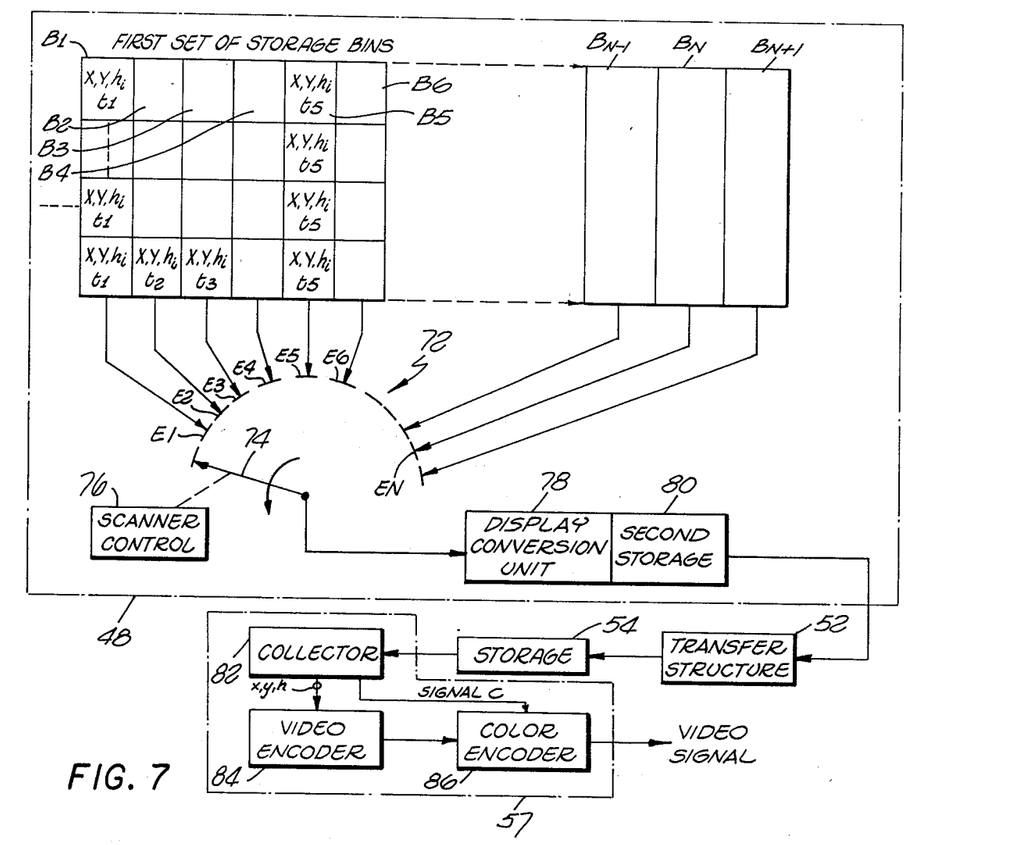
FIG. 7 is a detailed block and schematic diagram of a portion of the system of FIG. 1.

Pursuing the explanation of the assumed occurrence (a single 18 hertz wave in a data slice) after presenting the data slice at the forefront of the box 22, processing is performed on the signals $x_i$, $y_i$ and $h_i$ according to the value of tr, to displace the slice rearward in the box. The appearance of a marching display is created by such repetitive processing of signals $x_i$, $y_i$ and $h_i$ to accomplish a rearward displacement in the box 22. Reference will now be made to FIG. 7 showing the structure of the working picture processor and memory storage 48 in somewhat greater detail in relation to other components of the system.

After the formation of $x_i$, $y_i$ and $h_i$ signals for the symbol of the foremost initial data slice, those signals are registered in one of a first plurality of memory storage bins B1—Bn+, as represented in FIG. 7. Specifically as illustrated, the signals depicting waves in the foremost (most recent) data slice may be registered in the bin Bn. The signals representative of the waves in the last-prior data slice are contained in the bin Bn−1; and so on. Of course, each data slice may indicate various numbers of waves, ranging from none to a substantial number. In that regard, for purposes of illustration, the oldest bin B1 is represented to contain signals for a substantial number of waves while the bins B4 and B6 are indicated to contain no wave signals.

The signals from each of the bins B1—Bn+ are scanned in counterclockwise (reverse numerical) sequence by a collector 72 illustrated in an electromechanical configuration for purposes of explanation. Of course, an electronic equivalent of such structure is utilized in the actual operating system. The collector 72 includes a plurality of stationary contacts (E1—En+) which are individually connected to receive signals from the similarly numbered bins B1—Bn+. A movable contact 74 engages the contacts E1—En+, driven by a scanner control 76 to deliver signals from the bins in reverse or descending numerical sequence, data slice by data slice.

The contact 74 supplies the representative signals $x_i$, $y_i$ and $h_i$ for each slice to a display conversion unit 78 (part of the working picture processor and memory storage 48 of FIG. 1) which performs the appropriate perspective conversion according to tr (the relative time associated with this bin) in order to determine the current location and height (x, y and h) as per FIG. 5. This unit is closely associated with a second set of storage bins 80. The contents of storage 80 is transferred by a direct memory access transfer structure 52 to the final storage 54 as indicated above. The contents of the storage 54 is then scanned by a collector 82 (functionally similar to the collector 72). The collector 82 along with the video encoder 84 and the color encoder 86 are incorporated in the scanner encoder 57 as represented in FIG. 1. The color signal c is also transferred to final storage 54. As a result of the scanning by collector 82, the color information is provided to the color encoder 86 at the same time the unblanking information is channeled to video encoder 84.

In the operation of the subsystem as illustrated in FIG. 7, the slice by slice timing sequence wherein slices gradually move rearward from the front of the display is accomplished by selective operation of the scanner control 76. Each of the storage bins B1—Bn contains slice data in the order in which they were received and therefore in reverse order of their perspective depths. However, with the formulation of a new data slice, say Bn+1, the bins will be scanned in a shifted order, which leaves out the contents of bin B1 (oldest data). Thus, the times tr associated with each bin change by one time step. That is, rather than to shift the contents of the bins B1—Bn, the scanner control 76 simply designates the scanning sequence of the contacts E1—En in such a sequence that each time a fresh slice is developed, the signals from adjacent bins (representing slices) are shifted in significance (i.e., tr associated with each bin changes); as a consequence, the oldest data slice is simply not sensed. In effect, the scanning is rotary so that the shift or displacement is accomplished simply by advancing the scanning of bins B1—Bn and contacts E1—En by one step each time a fresh slice of data is composed. Of course, in a rotary or circular configuration, as the bins of the oldest data slices are not scanned any longer, they become available for storage of the newest data.

As a result of the shifting operation, the signals assigned to bin B2, for example, will be at the rear of box 22 during one interval of display, then those assigned to bin B3 will be the last slice displayed when the next slice is received, then bin B4 takes the last place on occurrence of the following slice. Consequently, the collector 72 functions to shift the slices in timed significance bringing in front of the picture the most recent slice and ignoring the oldest slice of the previous scanning (display) period.

The signals $x_i$, $y_i$, and $h_i$ received from the memory storage bins B1—Bn by the unit 78 (FIG. 7) are processed in two ways. First, the signals are processed to reflect rearward displacement in the box 22. As the symbols represented by the signals are displaced slice-by-slice in the box 22, they are altered to reflect the perspective changes of displacement. That is, depending upon the time relative to the most recent slice, the signals x, y and h in the slice will be modified as illustrated in FIG. 5. As the relative time (and slice position) advance, the symbol becomes older and is shortened (h) and displaced (x and y). These modifications to the signals x, y, and h simply involve operation of arithmetic circuits to accommodate each set of signals of a slice to the relative position in box 22 in which it is to be displayed. Arithmetic units for accomplishing such changes are well known to the prior art, and any of the variety of such structures may be embodied in the conversion unit 78.

The other processing operation performed in the unit 78 involves translating the order of the individual symbols to the sequence in which they appear in the raster scan pattern of the television monitor 16. Of course, various techniques can be employed to accomplish the transformation utilizing well-known data processing apparatus. Specifically for example, a block of storage bins of the second storage 80 can be allocated to each scan line. These blocks are further arranged in the order in which the scan lines are displayed in the television raster pattern. Then, each symbol can be placed on a particular scan line determined by the x coordinate of the symbol, and stored in the mentioned block of storage bins. The position of the base of the symbol is determined by the y coordinate and is also stored. That is, the signals for the symbol are arranged for access in the order of their appearance in the television raster pattern.

It is not deemed appropriate to complicate this explanation by a discussion of the separate fields in the television display; however, as will be readily apparent to those skilled in the television arts, the two fields may be readily accommodated to accomplish the desired orderly arrangement of base points for individual symbols.

Upon completion of the processed signals, x and y, defining the base points (e.g. 64, FIG. 6) in their order of appearance in the scanning pattern and reflecting displacement in the perspective box 22, as developed by conversion unit 78 and saved in the storage 80, they are rapidly transferred along with the height signals h and color signal c through the structure 52 to the final storage 54. From that location, collector 82 scans the signals for transfer to the video encoder 84 which formulates the video signal for unblanking the beam as it traverses the height h of the symbol starting at the defined base point.

The video signal is further refined by the encoder 86 to accommodate a color presentation as described above. Thus, the system accomplishes a dynamic display of marching symbols 24 (FIG. 1) in the graphic perspective box 22 to reveal data in a readily perceivable form.

It may now be appreciated that the orientation of the display with the symbols 24 (FIG. 1) aligned on the individual scan lines of the television raster pattern provides a clear display with good definition. As the display is traced out in the raster pattern by the television monitor 16, the symbols (in the forms of lines or bars) are defined during intervals when the beam is unblanked. Specifically, when the scanning reaches the location of a symbol base point (see 64, FIG. 6, defined by x and y) the beam is unblanked and keyed with the appropriate color. The symbol is then formed until the beam is displaced to the extent indicated by the height signal h. Each of the symbols in the display are so formed to trace out the complete display in the field of reference.

Generally, the problems associated with the effective graphic display of data using conventional television techniques is recognized and considered in a book "Principles of Interactive Computer Graphics" by W. M. Newman and R. F. Sproul, published in 1973 by McGraw-Hill Inc. Not only does the present system overcome such difficulties but the symbols avoid the undesirable "staircase" and "dot" effects which frequently appear in symbols representative of data when developed in television displays.

As explained in detail above, the system of FIG. 1 has been embodied in an operating embodiment for the effective and informative display of EEG data. Recognizing the EEG as a continuous wave form, the system essentially windows the data in a moving configuration so that a display may either be in real time or afford effective review of an EEG record. As the term is employed in the field of computer graphics, windowing generally relates to the selective display of data. A detailed treatment of windowing is provided in the above-referenced book, "Principles of Interactive Computer Graphics." In that regard, systems of the present invention may be variously utilized for the selective display of a wide variety of different data forms. Such selective display or progressive windowing may or may not involve control of the picture motion by an independent variable, e.g., time. The system may be effectively employed to display complex data of a number of dimensions with window control to reveal changes in at least one of the dimensions. To illustrate a somewhat general case of the system, reference will now be made to FIG. 8.

An input generator 88 provides electrical signals representative of data, which signals are screened by a selector 90. Specifically, the selector 90 may take form of any variety of filters or other selection devices to delete predetermined data information. Alternatively, the selector 90 may simply be a coupling circuit for passing data onto a storage unit 92. The selector 90 may incorporate structure for providing data in a triad form and in that sense the brain wave analyzer system 34 of FIG. 1 is exemplary. Thus, the output from the selector 90 to the storage unit 92 is in the form of data elements, e.g., data triads which manifest the dimensions of individual data elements.

Figure 8:
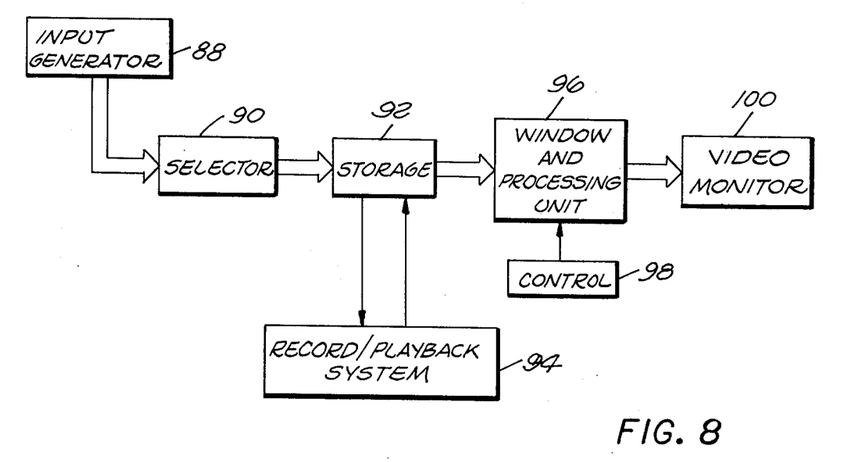
FIG. 8 is a block diagram of a somewhat generalized form of a system constructed in accordance with the present invention.

The storage 92 is coupled to a long-term storage system 94 which may take the form of a magnetic tape unit. Specifically, data signals e.g., triad signals, may be transferred from the storage 92 to the record-playback system 94 for display at a subsequent time.

The storage 92 supplies data signals to a window and processing unit 96 which is associated with a control apparatus 98. Functionally, the unit 96 processes signals representative of the data elements to accomplish the form of presentation and the window or fragment of presentation. In that regard, the unit 96 incorporates equivalent structure to that set forth in FIG. 7 above for providing signals representative of data elements which are contained in the sequence of a raster display utilized by a monitor 100. This unit translates digital format signals into a video signal for driving the monitor 100. Thus, the system as represented in FIG. 8 symbolizes the operation of converting data to digital elemental form, windowing the data progressively for display and aligning the data in the sequence of a raster scan so as to accomplish a display of symbols as disclosed in an exemplary format above.

In view of the above, it may be seen that the system of the present invention as disclosed herein will develop a dynamic display to manifest a substantial quantity of complex data. A substantial interval of data may be treated, for example, in real time, with the display effectively manifesting the time sequence. Of course, as explained above, the display is of relatively high quality in view of the manner in which the television monitor is utilized within the system. However, it should be recognized that the system may be variously embodied with widely varying possibilities for utilization of different structures and techniques. Consequently, it is understood that the scope hereof should be determined in accordance with the claims as set forth below.

What is claimed is:

1. A display system for data events characterized in at least three dimensions, and represented by electrical signals, one of said dimensions being of an independent variable, other dimensions being dependent variables, comprising:
    a plane display device for selectively displaying images as traced thereon;
    means defining a dimensioned field of reference for said display device, said field referencing said three dimensions characterizing said data events in accordance with the display thereof and defining an origin location with respect to said independent variable;
    first means for processing said electrical signals to provide display signals for actuating said display device to display symbols indicating the other dimensions of said data events and referenced to the origin location of said field of reference with respect to said independent variable; and
    second means for processing said display signals to shift the display thereof by said display device along the independent variable dimension of said field of reference to provide a dynamic display changing with reference to said origin location with said independent variable.

2. A display system according to claim 1 wherein said display device comprises a raster-pattern scan device and wherein one of said other dimensions is scaled to said field parallel to said raster pattern whereby scanning lines of said raster pattern align with said display symbols as generally parallel lines.

3. A display system according to claim 2 further including a storage register means and means for storing said display signals in said storage register means in an access order coinciding to the order of presentation in said raster pattern of represented symbols.

4. A display system according to claim 2 wherein said display device comprises a color television monitor and further including means to color code said represented symbols according to one of said variables.

5. A display system according to claim 1 wherein said field of reference is defined as three-dimensional perspective box and wherein the depth dimension of said box references the independent variable.

6. A display system according to claim 5 further including means to actuate said display device to display said perspective box.

7. A display system according to claim 5 wherein said display device comprises a raster-pattern scan device and wherein one of said other dimensions is scaled to said field parallel to said raster pattern whereby scanning lines of said raster pattern align with said display symbols as generally parallel lines.

8. A display system for data elements characterized in at least three dimensions and represented by electrical signals, comprising:
    a plane display device for selectively displaying images as traced thereon;
    means defining a field of reference for said display device, said field referencing said three dimensions characterizing said data events, and defining a box of three dimensions;
    means for processing said electrical signals to provide display signals for activating said display device to form line symbols with respect to said box to manifest said data elements;
    and means for progressively windowing said display signals to said display means to activate said display means for exhibiting a dynamic display of said line symbols.

9. A display system to represent discrete data events each characterized by a triad of magnitudes in the form of linear symbols originating on a two-dimensional virtual surface and scaled in a third dimension of a reference system, comprising:
    display means to produce a visible image in accordance with electrical image signals;
    storage means to temporarily store triads of values;
    means to receive, modify and delete the values of said triads of magnitudes from said storage means; and
    processor means including a processing unit and memory to repeatedly generate said electrical image signals from said triads of values stored in said storage means (i) by positioning the origin of said linear symbols on said two-dimensional virtual surface according to the first two values of each said triad and by scaling the length of said symbol into the third dimension according to the third value (ii) by altering according to perspective the length in one dimension and the position in at least one of the other two dimensions of each symbol, and (iii) by limiting the number of displayed symbols to include only those events characterized by triads defining the originating point on said virtual surface within a predetermined twodimensional display range.

10. A system according to claim 9 where the limits of said two-dimensional display range are altered at various intervals of time thereby resulting in the display of a sequence of slightly different pictures to create the illusion of motion.

11. A system according to claim 10 where said alterations of display range limits are periodic and where during each display period said display range includes triads newly stored in said storage means during the immediately preceding period and excludes a like period of oldest-stored triads.

12. A display system according to claim 9 where said discrete events are further separated in a fourth dimension by assigning various colors to said linear symbols representing them and which further includes:
storage means capable to store a color-defining fourth value appended to each of said triads of values;
means to receive and store said fourth value in, and means to delete it from, said storage means; and
processor means which additionally generate electrical image signals with color-defining elements in accordance with said fourth value.

13. A display system according to claim 9 where a fourth display dimension is manifest as a color assigned to each of said linear symbols and which further includes processor means capable of assigning said color according to the information contained in said triads of values and to predetermined arbitrary criteria.

14. A system according to claim 12 where the limits of said two-dimensional display range are altered at various intervals of time thereby resulting in the display of a sequence of slightly different pictures to create the illusion of motion.

15. A system according to claim 14 where said alterations of display range limits are periodic and where during each display period said display range includes values newly stored in said storage means during the immediately preceding period and excludes a like period of oldest-stored values.

16. A system according to claim 11 where said discrete events are EEG waves of which the period and time of occurrence define the originating point of said symbols on said virtual two-dimensional surface and the amplitude defines the length in the third dimension.

17. A system according to claim 15 where said discrete events are EEG waves of which the period and time of occurrence define the originating point of said symbols on said virtual two-dimensional surface and the amplitude defines the length in the third dimension.

18. A system according to claim 17 where said processor means separate several ranges in one dimension of said two-dimensional virtual surface and assigns a color to all symbols originating in the same range for easier visual separation of originating points.

19. A system according to claim 18 where said ranges are separated in the horizontal dimension and where the period of said EEG waves is scaled in the same dimension and the time of occurrence is scaled in the depth dimension.

20. A system according to claim 9 further including means to generate additional image signals to result in a reference system to be displayed by said display means simultaneously with symbols representing said discrete events.

21. A system according to claim 9 further including means to record from and play back into said storage means upon command.

* * * * *